US007491524B2

(12) United States Patent
Crooke

(10) Patent No.: US 7,491,524 B2
(45) Date of Patent: Feb. 17, 2009

(54) HUMAN RNASE III AND COMPOSITIONS AND USES THEREOF

(75) Inventor: Stanley T. Crooke, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 319 days.

(21) Appl. No.: 11/001,993

(22) Filed: Dec. 2, 2004

(65) Prior Publication Data

US 2005/0159384 A1 Jul. 21, 2005

Related U.S. Application Data

(60) Division of application No. 10/079,185, filed on Feb. 20, 2002, now abandoned, which is a continuation-in-part of application No. 09/900,425, filed on Jul. 6, 2001, now Pat. No. 6,737,512.

(51) Int. Cl.
| | |
|---|---|
| C12N 9/00 | (2006.01) |
| C12N 9/22 | (2006.01) |
| C12N 15/00 | (2006.01) |
| C12N 15/08 | (2006.01) |
| A61K 38/43 | (2006.01) |
| C12Q 1/68 | (2006.01) |

(52) U.S. Cl. ............................. 435/199; 435/6; 435/183; 435/455; 435/440; 424/94.1

(58) Field of Classification Search ...................... 436/6, 436/7.1; 514/44; 536/24.1, 24.5; 530/350, 530/300

See application file for complete search history.

(56) References Cited

U.S. PATENT DOCUMENTS

| | | | | |
|---|---|---|---|---|
| 5,804,683 | A | 9/1998 | Usman et al. | 536/25.31 |
| 5,891,683 | A | 4/1999 | Usman et al. | 435/91.31 |
| 5,898,031 | A | 4/1999 | Crooke | 435/172.3 |
| 6,107,094 | A | 8/2000 | Crooke | 435/455 |
| 6,506,559 | B1 | 1/2003 | Fire et al. | |

FOREIGN PATENT DOCUMENTS

| | | |
|---|---|---|
| EP | 0 649 467 B1 | 9/1998 |
| EP | 1 284 298 | 2/2003 |
| WO | WO 92/07065 | 4/1992 |
| WO | WO 94/01550 | 1/1994 |
| WO | WO 97/46570 | 12/1997 |

OTHER PUBLICATIONS

Database EMBL, "Homo sapiens Ribonuclease III mRNA," Accession No. AFI89011, (2000).
Chanfreau et al., "Alternative 3' -end processing of U5 snRNA by Rnase III," *Genes and Devel.*, 1997, 11, 2741-2751.
Court, D., "RNA Processing and Degradation by Rnase III," *Control of Messenger RNA Stability*, 1993, Academic Press, Inc., Belasco and Brawerman, eds., 71-116.
Elbashir et al., "RNA interference is mediated by 21-and 22-nucleotide RNAs," *Genes and Devel.*, 2001, 15, 188-200.
Elbashir et al., "Duplexes of 21-nucleotide RNAs mediate RNA interference in cultured mammalian cells," *Nature*, 2001, 411, 494-498.
Elela et al., "Rnase III Cleaves Eukaryotic Preribosomal RNA at a U3 snoRNP-Dependent Site," *Cell*, 1996, 85, 115-124.
Mian, I. S., "Comparative sequence analysis of ribonucleases HII, III, II, PH and D," *Nucleic Acids Res*, 1997, 25, 3187-3195.
Qu et al., "Seven Novel Methylation Guide Small Nucleolar RNAs are Processed from a Common Polycistronic Transcript by Rat1p and Rnase III in Yeast," *Mol Cell Biol*, 1999, 19(2), 1144-1158.
Wu et al., "Identification and Partial Purification of Human Double Strand Rnase Activity," *J Biol Chem*, 1998, 273(5), 2532-2542.
Arya, S. K. et al., "Inhibition of RNA Directed DNA Polymerase of Murine Leukemia Virus by 2'-O-Alkylated Polyadenylic Acids," *Biochem Biophys Res Commun*, 1974, 59(2), 608-615.
Arya, S. K. et al., "Inhibition of Synthesis of Murine Leukemia Virus in Cultured Cells by Polyribonucleotides and Their 2'-O-Alkyl Derivatives," *Molecular Pharmacology*, 1976, 12, 234-241.
DeClercq, E. et al., "Influence of various 2- and 2'-substituted polyadenyl acids on murine leukemia virus reverse transcriptase," *Cancer Letters*, 1979, 7, 27-37.
Hobbs, J. et al., "Polynucleotides Containing 2'-Amino 2'-deoxyribose and 2'-Azido-2'-deoxyribose," *Biochem.*, 1973, 12, 5138-5145.
Hobbs, J. et al., "Poly 2'-Deoxy-2'-Aminouridylic Acid," *Biochem Biophys Res Commun* 1972, 46(4), 1509-1515.
Hobbs, J. et al., "Polynucleotides Containing 2'-Chloro-2'-deoxyribose," *Biochem.*, Eckstein et al., Ed., 1972, 11, 4336-4344.
Pieken, W. et al., "Kinetic Characterization of Ribonuclease-Resistant 2'-Modified Hammerhead Ribozymes," *Science*, 1991, 253, 314-317.
Pilet, J. et al., "Structural parameters of single and double helical polyribonucleotides," *Biochem Biophys Res Commun*, 1973, 52(2), 517-523.
Rottman, F. et al., "Polynucleotides Containing 2'-O-Methyladenosine. I. Synthesis by Polynucleotide Phosphorylase," *Biochem*, 1968, 7, 2634-2641.
Rottman, F. et al., "Polymers Containing 2'-O-Methylnucleotides. II. Synthesis of Heteropolymers," *Biochem*, 1969, 8(11), 4354-4361.
Wincott et al., "Synthesis, deprotection, analysis and purification of RNA and ribozymes," *Nucl. Acids Res.*, 1995, 23(14), 2677-2684.
Zmudzka, B. et al., "Poly 2'-O-methylcytidylic acid and the role of the 2'-hydroxyl in polynucleotide structure," *Biochem Biophys Res Commun*, 1969, 37(6), 895-901.
Wu et al., "Human RNase III Is A 160-kDa Protein Involved In Preribosomal RNA Processing," *J. Biol. Chem.*, 2000, 275:36957-36965.
Krinke et al., "The Cleavage Specificity Of RNase III," *Nucleic Acids Res.*, 1990, 18:4809-4815.
International Search Report for PCT/US2003/004912 dated Nov. 19, 2003.

*Primary Examiner*—Sean R McGarry
(74) *Attorney, Agent, or Firm*—Isis Patent Department

(57) ABSTRACT

The present invention provides polynucleotides encoding human RNase III and polypeptides encoded thereby. Methods of using said polynucleotides and polypeptides are also provided.

6 Claims, 2 Drawing Sheets

```
Human  PVIQKLTEFEEAIGVIFTHVRLLARAFTLRTVGFNHLTL---GHNQRMEFLGDSIMQLVATEYLFIRFPDHHRGHLTLLRSSLVNNRTQAKVAEELGMQE
Worm   PTLSTFHALEERLGIQFNNIRLLAKAFTRRNIPNNDLTK---GHNQRLEWLGDSVLQLIVSDFLYRFPYHHEGHMSLLRTSLVSNQTQAVVCDDLGFTE
PAC    GEYPPPLPLRSEKLKEQVFMHISRAYEIYPNQSNPNELLDIHNERLEFLGDSFFNLFTTRIIFSKFPQMDEGSLSKLRAKFVGNESADKFARLYGFDK
RNT    KATKWPPKLPEIQDLAIRARVFIHKSTIKDKVYLSGSEMINAHNERLEFLGDSILNSVMTLIIYNKFPDYSEGQLSTLRMNLVSNEQIKQWSIMYNFHE
RNC    MNPIVINRLQRKLGYTFNHQELLQQALTHRSASS------KHNERLEFLGDSILSYVIANALYHRFPRVDEGDMSRMRATLVRGNTLAELAREFELGE Human  YAITNDKTKRPV----GLRTKTLADLLESFIAALYTDKDLEFVHTF-MNVCFFPRLKEFILNQDWNDPKSQLQQCCLTLRTE------GKEPDIPLYKT
Worm   FVIK-APYKTPE------LKLKDKADLVEAFIGALYVDRGIEHCRAF-IRIVFCPRLKHFIESEKWNDAKSHLQQWCLAMRDP-----SSSEPDMPEYRV
PAC    TLVLSYSAEKDQ----LRKSQKVIADTFEAYLGALILDGQEETAFQWVSRLLQPKIANITVQRPIDKLAKSKLFHKYSTL--------GHIEYRW
RNT    KLKTNFDLKDENSNFQNGKLKLYADVFEAYIGGLMEDDPRNNLPK--IRKWLRKLAKPVIESATRNQVALEKTDKLDMNAKRQLYSLIGYASLRLHYVT
RNC    CLRLGPGELKSG---GFRRESILADTVEALIGGVFLDSDIQTVEKL-ILNWYQTRLDEISPGDKQKDPKTRLQEYLQ---------GRHLPLPTYLV Human  LQTVGPSHARTYTV-AVYFKGERIGCGKGPSIQQAEMGAAMDALEKYNFPQMAHQKRFIGRKYRQELKEMRWEREHQEREPDETEDIKK (end1374)
Worm   LGIEGPTNNRIFKI-AVYYKGKRLASAAESNVHKAELRVAELALANLESMSFSKMKAKNNSMRRRLSQDTSD (end412)
PAC    VDGAGGSABGYVI--ACIFNGKEVARAWGANQKDAGSRAAMQALEVLAKDYSKFAR (end363)
RNT    VKKPTAVDPNSIVE-CRVGDGTVLGTGVGRNIKIAGIRAAENALRDKKMLDFYAKQRAAIPRSESVLKDPSQKNKKRKFSDTS (end471)
RNC    VQVRGEAHDQEFTIHCQVSGLSEPVVGTGSSRRKAEQAAAEQALKKLELE (end226)
```

FIGURE 1

```
Human                                                                                         MMQGNTCHRMSFHPGRGCPRGR
Human    GGHGARPSAPSFRPQNLRLLHPQQPPVQYQYEPPSAPSTTFSNSPAPNFLPPRPDFVPFPPPMPPSAQGPLPPCPIRPFPFPNHQMRHPFPVPPCFPPMP
Human    PPMPCPNNPPVPGAPPGQGTFPFMMPPPSMPHPPPPPVMPQQVNYQYPPGYSHHNFPPPSFNSFQNNPSSFLPSANNSSPHFRHLPPYPLPKAPSERR
Human    SPERLKHYDDHRHRDHSHGRGERHRSLDRRERGRSPDRRRQDSRYRSDYDRGRTPSRHRSYERSRERERHRDNRRSPSLERSYKKEYKRSGRSYG
Human    LSVVPEPAGCTPELPGEIIKNTDSWAPPLEIVNHRSPSREKKRARWEEEKDRWSDNQSSGKDKNYTSIKEKEPEETMPDKNEEEEELLKPVWIRCTHS
Human    ENYYSSDPMDQVGDSTVVGTSRLRDLYDKFEEELGSRQEKAKAARPPWEPPKTKLDEDLESSESECESDEDSTCSSSSDSEVFDVIAEIKRKKAHPDR
Human    LHDELWYNDPGQMNDGPLCKCSAKARRTGIRHSIYPGEEAIKPCRPMTNNAGRLFHYRITVSPPTNFLTDRPTVIEYDDHEYIFEGFSMPAHAPLTNIP
Human    LCKVIRFNIDYTIHFIEEMMPENFCVKGLELFSLFLFRDILELYDMNLKGPLFEDSPPCCPRFHFMPRFVRFLPDGGKEVLSMHQILLYLLRCSKALVP
Human    EEEIANMLQWEELEWQKYAEECKGMIVTNPGTKPSSVRIDQLDREQFNPDVITFPIIVHFGIRPAQLSYAGDPQYQKLWKSYVKLRHLLANSPKVKQTD
Human    KQKLAQREEALQKIRQKNTMRREVTVELSSQGFWKTGIRSDVCQHAMMLPVLTHHIRYHQCLMHLDKLIGYTFQDRCLLQLAMTHPSHHLNFGMNPDHA Human    RNSLSNCGIRQPKYGDRKVHHMMRKKGINTLINIMSRLGQDDPTPS--RINHNERLEFLGDAVVEFLTSVHLYYLFPSLEBGGLATYRTAIVQNQHLA
Worm     MSLFNIMKGTSGGEPILHNERLEYLGDAVVELIVSHHLYFMLTHHFBGGLATYRTALVQNRNLA
PAC                                                                  MGRFKRHHEGDSDSSSASDSLSRGRRSLGHKRSSHIKNRQYY
RNT                                                                  MGSKVAGKKKTQNDNKLDNENGSQQRENINTKTLLKGNLKISNYKYLEVIQLEHAVTKLVESYNKIIELSPNLVAYNEAVNNQDRVPVQILPSLSRYQL Human    MLAKKLE-LDPFML-YAHGPDLCRESDLRHAMANCFEALIGAVYLEGSLEEAKQLFG---RLL-FNDPDLREVWLNYPLHPL-Q-LQEPNTDRQLIETS
Worm     TLAKNCR-IDE-MLQYSHGADLINVAEFKHALANAFEAVMAAIYLDGGLAPCDVIFS---KAMYGHQPVLKEKWDHINEHEL--KREDPQGDRDLSFIT
PAC      ILEKKIRKLMFAMKALLEETKHST------KDDVNLVIPGSTWSHIEGVYEMLKSRHDRQNEPVIEEPSSHPKNQKNQENNEPTSEFEE
RNT      KLAAELKTLHDLKKDAILTEITDYENEFDTEQKQ------PILQEISKADMEKLEKLEQVKREKREKIDVNVYENLNEKEDEEEDEGEDSYDPTKAGDIV
```

FIGURE 1 (Continued)

HUMAN RNASE III AND COMPOSITIONS AND USES THEREOF

CROSS-REFERENCE TO RELATED APPLICATIONS

The present application is a divisional of U.S. application Ser. No. 10/079,185 filed Feb. 20, 2002, now abandoned which is a continuation-in-part of U.S. application Ser. No. 09/900,425 filed Jul. 6, 2001, U.S. Pat. No. 6,737,512. All of the above are assigned to the assignee of the present invention and are incorporated by reference herein in their entirety.

FIELD OF THE INVENTION

The present invention relates to a human RNase III, the gene for which has now been cloned and characterized, and compositions and uses thereof. Antisense inhibitors of human RNase III are also described.

BACKGROUND OF THE INVENTION

Ribonuclease III (RNase III) is an endoribonuclease that cleaves double stranded RNA. The enzyme is expressed in many organisms and is highly conserved. I. S. Mian, *Nucleic Acids Res.*, 1997, 25, 3187-95. All RNase III species cloned to date contain an RNase III signature sequence and vary in size from 25 to 50 kDa. Multiple functions have been ascribed to RNase III. In both *E. coli* and *S. cerevisiae*, RNase III has been reported to be involved in the processing of pre-ribosomal RNA (pre-rRNA). Elela et al., *Cell*, 1996, 85, 115-24. RNase III has also been reported to be involved in the processing of small molecular weight nuclear RNAs (snRNAs) and small molecular weight nucleolar RNAs (snoRNAs) in *S. cerevisiae*. Chanfreau et al., *Genes Dev.* 1996, 11, 2741-51; Qu et al., *Mol. Cell. Biol.* 1996, 19, 1144-58. In *E. coli*, RNase III has also been reported to be involved in the degradation of some mRNA species. D. Court, in *Control of messenger RNA stability*, 1993, Academic Press, Inc, pp. 71-116.

A human double strand RNase (dsRNase) activity has been described. Wu et al., *J.Biol. Chem.*, 1998, 273, 2532-2542; Crooke, U.S. Pat. No. 5,898,031; U.S. Pat. No. 6,107,094. By the rational design and testing of chemically modified antisense oligonucleotides that contained oligoribonucleotide stretches of varying length, a dsRNase activity was demonstrated in human T24 bladder carcinoma cells which produced 5'-phosphate and 3'-hydroxyl termini upon cleavage of the complementary cellular RNA target. This pattern of cleavage products is a feature of *E. coli* RNase III. The cleavage activity in human cells required the formation of a dsRNA region in the oligonucleotide. This human dsRNase activity is believed to be useful as an alternative terminating mechanism to RNase H for antisense therapeutics. Because it relies on "RNA-like" oligonucleotides, which generally have higher potency than the "DNA-like" oligonucleotides required for RNase H activity, it may prove an attractive alternative to RNase H-based antisense approaches.

RNA interference (RNAi) is a form of sequence-specific, post-transcriptional gene silencing in animals and plants, elicited by double-stranded RNA (dsRNA) that is homologous in sequence to the silenced gene. Elbashir et al., *Nature*, 2001, 411, 494-498. dsRNA triggers the specific degradation of homologous RNAs, only within the region of homology. The dsRNA is processed to 21- to 23-nucleotide fragments, sometimes called short interfering RNAs (siRNAs) which are believed to be the guide fragments for sequence-specific mRNA degradation. The processing of longer dsRNA to these short siRNA fragments is believed to be accomplished by RNase III. Elbashir et al., ibid., Elbashir et al., *Genes and Devel.*, 2001, 15, 188-200. Thus it is believed that the human RNase III of the present invention may be useful in further understanding and exploiting the gene silencing mechanism, particularly in human cells.

Despite the substantial information about members of the RNase III family and the cloning of genes encoding proteins with RNase III activity from a number of lower organisms (*E. coli*, yeast and others), no human RNase III has previously been cloned. This has hampered efforts to understand the structure of the enzyme(s), its distribution and the functions it may serve. The present application describes the cloning and characterization of a cDNA that expresses a human RNase III. Cloning and sequencing of the cDNA encoding human RNase III allowed characterization of this nucleic acid as well as of the location and function of the RNase III protein itself.

SUMMARY OF THE INVENTION

The present invention provides a polynucleotide sequence (set forth herein as SEQ ID NO: 1) which has been identified as encoding human RNase III by the homology of the calculated expressed polypeptide (provided herein as SEQ ID NO: 2) with known amino acid sequences of yeast and worm RNase III as well as by functional analysis.

The present invention provides polynucleotides that encode human RNase III, the human RNase III polypeptide, vectors comprising nucleic acids encoding human RNase III, host cells containing such vectors, antibodies targeted to human RNase III, nucleic acid probes capable of hybridizing to a nucleic acid encoding a human RNase III polypeptide, and antisense inhibitors of RNase III expression. Methods of inhibiting RNase III expression or activity are also provided, as are pharmaceutical compositions which include a human RNase III polypeptide, an antisense inhibitor of RNase III expression, or a vector containing a nucleic acid encoding human RNase III.

Methods for identifying agents which modulate activity and/or levels of human RNase III are also provided. Methods of promoting inhibition of expression of a selected protein via antisense, methods of screening oligonucleotides to identify active antisense oligonucleotides against a particular target, methods of prognosticating efficacy of antisense therapy, methods of promoting RNA interference (RNAi) or other forms of gene silencing in a cell and methods of eliciting cleavage or modification of a selected cellular RNA target are also provided. All of these methods exploit the RNA-binding and cleaving activity of RNase III polypeptides. In preferred embodiments the polynucleotides used in these methods are RNA-like oligonucleotides. Also provided are methods of identifying agents which increase or decrease activity or levels of human RNase III.

The compositions and methods of the present invention are useful for research, biological and clinical purposes. For example, the methods, polynucleotides and antisense oligonucleotides are useful in defining the roles of RNase III and the interaction of human RNase III and cellular RNA (including pre-mRNA or pre-rRNA).

BRIEF DESCRIPTION OF THE DRAWINGS

FIG. 1 shows the amino acid sequence of human RNase III (SEQ ID NO: 2) and a comparison of the sequence of the RNase III domain of the human RNase III to RNase III domains of *C. elegans* (Worm; SEQ ID NO: 3), *S. pombe* (PAC; SEQ ID NO: 4) and *S. cerevisiae* (RNT; SEQ ID NO:

5) and *E. coli* (RNC; SEQ ID NO: 6). Bold letters: identical amino acids of human RNase III to other species. @@@: putative catalytic center. HHH: alpha helix; BBB: beta sheet (dsRNA binding region at C-terminus). Amino acid identity of human RNase III to Worm (41%), PAC (17%), RNT (15%) and RNC (16%). *: Potential phosphorylation sites analyzed using OMIGA (Oxford Molecular Ltd.).

DETAILED DESCRIPTION OF THE INVENTION

A cDNA encoding human RNase III has now been cloned and characterized. The cloned sequence is provided herein as SEQ ID NO: 1. This cDNA encodes a protein of 160 kDa which is ubiquitously expressed in human cell and tissue types, and is involved in processing of preribosomal RNA (pre-rRNA).

Thus, in accordance with one aspect of the present invention, there are provided isolated polynucleotides which encode human RNase III polypeptides. By "polynucleotides" it is meant to include any form of RNA or DNA such as mRNA, pre-mRNA or cDNA or genomic DNA, respectively, obtained by cloning or produced synthetically by well known chemical techniques. The term "polynucleotide" is also meant to include oligonucleotides, e.g. synthetic antisense oligonucleotides. DNA or RNA polynucleotides may be double- or single-stranded. Single-stranded DNA or RNA polynucleotides may comprise the coding or sense strand or the non-coding or antisense strand.

Methods of isolating a polynucleotide of the present invention via cloning techniques are well known. For example, to obtain the polynucleotide sequence of SEQ ID NO: 1, a similarity search of the yeast RNT1 gene (RNase III, Genbank accession no. AAB04172; SEQ ID NO: 5) and the *Caenorhabditis elegans* RNase III gene (Genbank accession no. 001326; SEQ ID NO: 3) with the XREF database (National Center for Biotechnology Information, NIH, Rockville Md.) was performed. A 393 base pair (bp) human EST clone (GenBank AA083888) was identified.

Using primers based on this EST sequence, a clone (U4) corresponding to the COOH-terminal portion of the protein (nucleotides 3569-4764 of full length cDNA) was cloned by 3' RACE. Eight positive clones were isolated by screening a liver cDNA library with this clone. With primers based on one of these clones, 5' RACE was performed to clone a cDNA of approximately 1 kb, which corresponds to the middle part of the full length cDNA. In the same way, a cDNA of the $NH_2$-terminal portion was cloned. Primers based on the $NH_2$-terminal-most clone were used to perform additional 5'-RACE to obtain the $NH_2$-terminal portion of the cDNA. The overlapping clones were sequenced and assembled to a full length human RNase III cDNA with a total of 4764 nucleotides. This human RNase III polynucleotide sequence is provided herein as SEQ ID NO: 1 and has been deposited as GenBank accession no. AF189011. The cDNA contained a coding sequence of 4125 nucleotides (from 246-4370 of SEQ ID NO: 1) that was calculated to encode a 1374 amino acid protein. This polypeptide sequence is provided herein as SEQ ID NO: 2, shown in FIG. 1. The calculated molecular weight of the protein is 160 kDa based on the prediction of the first translated methionine as the translation initiation site. Northern hybridization analyses demonstrated that the human RNase III mRNA was approximately 5 kb in size. It was found to be ubiquitously expressed in human tissues and cell lines. Compared to *C. elegans*, yeast and bacterial RNase III, human RNase III is substantially larger and contains multiple domains. The RNase III domain (amino acids 949-1374) is located at the carboxy terminus of the protein and is homologous to *C. elegans*, yeast and bacterial RNase III. The human RNase also contains proline rich (amino acids 1-220) and serine-arginine rich (amino acids 221-470) domains near the amino terminus. The SR and RNase III domains are separated by 478 amino acids.

The RNase III domain of human RNase III is conserved with other species and is most homologous with *C. elegans* RNase III (41% identity). Both the human RNase III domain and *C. elegans* RNase III contain two RNase III signature sequences (HNERLEFLGDS; SEQ ID NO 7). Sequence identity was also compared with the yeasts *S. pombe* (PAC gene)(17% homology) and *S. cerevisiae* (RNT gene) (15% homology) and with *E. coli* RNase III (RNC gene) (16% homology). Human RNase III also contains multiple phosphorylation sites. The SR domain is usually present in SR or SR related proteins that play crucial roles in mRNA splicing. The fusion of SR and RNase III domains into a single protein suggests that human RNase III may be involved in a number of RNA metabolic events. The presence of multiple potential phosphorylation sites suggests that the enzyme is regulated by phosphorylation.

As used herein, the phrase "homologous nucleotide sequence," or "homologous amino acid sequence," or variations thereof, refers to sequences characterized by a homology, at the nucleotide level or amino acid level, of at least the specified percentage. Homologous nucleotide sequences include those sequences coding for isoforms of proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a protein of a species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding other known RNase IIIs. Homologous amino acid sequences include those amino acid sequences which contain conservative amino acid substitutions and which polypeptides have the same binding and/or activity. A homologous amino acid sequence does not, however, include the amino acid sequence encoding other known RNase IIIs. Percent homology can be determined by, for example, the Gap program (Wisconsin Sequence Analysis Package, Version 8 for Unix, Genetics Computer Group, University Research Park, Madison Wis.), using the default settings, which uses the algorithm of Smith and Waterman (Adv. Appl. Math., 1981, 2, 482-489, which is incorporated herein by reference in its entirety).

In a preferred embodiment, the polynucleotide of the present invention comprises the nucleic acid sequence of SEQ ID NO: 1. However, as will be obvious to those of skill in the art upon this disclosure, due to the degeneracy of the genetic code, polynucleotides of the present invention may comprise other nucleic acid sequences encoding the polypeptide of SEQ ID NO: 2 and derivatives, variants or active fragments thereof.

The invention further provides homologs of the human RNase III DNA. Such homologs, in general, share at least 50%, at least 60%, at least 65%, at least 70%, at least 75%, at least 80%, at least 85%, at least 90%, at least 95%, at least 98%, or at least 99% homology with the human RNase III DNA of the invention. Species homologs, sometimes referred to as "orthologs," in general, share at least 50%, at least 60%, at least 65%, at least 70%, at least 75%, at least 80%, at least 85%, at least 90%, at least 95%, at least 98%, or at least 99% homology with the human RNase III DNA of the invention. Generally, percent sequence "homology" with respect to polynucleotides of the invention can be calculated as the percentage of nucleotide bases in the candidate sequence that are identical to nucleotides in the human RNase III sequence set forth in the appended Sequence Listing, after aligning the sequences and introducing gaps, if necessary, to achieve the maximum percent sequence identity.

Another aspect of the present invention relates to the polypeptides encoded by the polynucleotides of the present invention. In a preferred embodiment, a polypeptide of the present invention comprises the deduced amino acid sequence of human RNase III provided in SEQ ID NO: 2. However, by "polypeptide" it is also meant to include fragments, derivatives and analogs of SEQ ID NO: 2 which retain essentially the same biological activity and/or function as human RNase III. Alternatively, polypeptides of the present invention may retain their ability to bind to double stranded RNA even though they do not function as active RNase III enzymes in other capacities. Thus an enzyme may "modify" its RNA substrate, e.g., bind and interfere with the function of the RNA but not cleave it, or may bind and cleave. In some embodiments cleavage is a preferred form of modification. In another embodiment, polypeptides of the present invention may retain nuclease activity but without specificity for an RNA/RNA duplex. Polypeptides of the present invention include recombinant polypeptides, isolated natural polypeptides and synthetic polypeptides, and fragments thereof which retain one or more of the activities described above.

The invention further provides homologs of the human RNase III polypeptide. Such homologs, in general, share at least 50%, at least 60%, at least 65%, at least 70%, at least 75%, at least 80%, at least 85%, at least 90%, at least 95%, at least 98%, or at least 99% homology with the RNase III polypeptides of the invention. Generally, percent sequence "homology" with respect to polypeptides of the invention can be calculated as the percentage of amino acid residues in the candidate sequence that are identical to amino acid residues in the RNAse III sequences set forth in the appended Sequence Listing, after aligning the sequences and introducing gaps, if necessary, to achieve the maximum percent sequence identity.

In some embodiments the present invention provides recombinant polypeptides that comprise RNase III domains from one or more organisms. Domains of RNase III that exhibit certain functions can be replaced with RNase III domains from other organisms that exhibit similar functions, while maintaining the overall function of the polypeptide. As a non-limiting example, a hybrid RNase III may comprise one or more *E. coli* RNase III domain, one or more *C. elegans* RNase III domain, and one or more human RNase III domain. As a non-limiting example, such hybrid RNase III polypeptides can be produced by first designing and producing recombinant DNA molecules encoding such polypeptides. Such recombinant DNA molecules are produced, for example, by replacing DNA sequences that encode individual domains in a polynucleotide encoding RNase III with DNA sequences from other organisms that encode RNase III domains that exhibit similar functions. The recombinant DNA construct thus produced can then be expressed and purified using means familiar to one of ordinary skill in the art.

To confirm the expression of the human RNase III protein, two anti-peptide antibodies were produced. The "anti-III" peptide antibody was derived from a peptide corresponding to amino acids 1356-1374 within the RNase III domain present in the C-terminal portion of the putative protein. The "anti-SR" peptide antibody was derived from a peptide corresponding to amino acids 266-284 within the SR-domain of the putative protein. Using these antibodies, Western blot analyses were performed to determine the size and localization of human RNase III. The anti-SR peptide antibody recognized a band in HeLa whole cell lysate with a molecular weight of approximately 160 kDa which is near the calculated protein size confirming that the full coding region is expressed in HeLa cells. Similar experiments were performed using different human cell lines e.g. A549, T24 and HL60 with equivalent results. To determine the localization of the protein, nuclear and non-nuclear fractions from HeLa cells and other human cell lines were prepared and equal amounts of proteins were analyzed by Western blots. RNase III was present primarily in the nuclear fractions. Non-nuclear fractions contained only trace amounts of protein, possibly due to the contamination during sample preparation. The anti-III peptide antibody gave results equivalent to those obtained with the anti-SR peptide antibody. To better understand the localization of human RNase III, the protein was identified in cells by indirect immunofluorescence microscopy. The nuclei of HeLa cells were stained by both anti-SR and anti-III antibodies, confirming that human RNase III is present in the nucleus. RNase III is localized extensively in nucleus and occasionally observed in nucleoli. This localization suggests possible involvement in both pre-mRNA and pre-rRNA processing. In *E. coli*, RNase III is associated with ribosomes in the cytoplasm. Robertson et al., *J. Biol. Chem,* 1968, 243, 82-91. Eukaryotic RNase III has not previously been shown to be localized in the nucleus.

The localization of human RNase III to nucleoli was found to be cell cycle regulated. Double thymidine treatment was used to synchronize HeLa cells to early-S phase. Two to four hours after releasing the thymidine block, HeLa cells entered S phase as determined by fluorescence activated cell sorting (FACS). Six to eight hours after release, HeLa cells entered the G2/M phase. There were no significant changes in the mRNA or protein levels of the RNase III during pre-S, S or G2/M phases. However, the subcellular localization of the protein changed during the cell cycle. When the cells were treated with thymidine and synchronized in early S phase, RNase III protein was present only in the nucleus and not the nucleoli, as determined by immunofluorescent labeling. After releasing from thymidine block, RNase III was translocated to nucleoli, reaching a peak at 4 hours when cells were in S phase. At that time, RNase III was present both in the nucleoli and the nucleus. The protein was present in the nucleoli for approximately 8 hours, and then disappeared from nucleoli as cells entered M phase. Localization of RNase III in the nucleoli was confirmed by double staining with an anti-nucleolin monoclonal antibody (MBL, Watertown, Mass.).

In human cells, nucleoli undergo phases of condensation and dissociation as a function of the cell cycle. Nucleoli dissociate upon entering prophase and disappear entirely during the late prophase and metaphase periods of mitosis, then begin to reappear during telophase and form dense organelles during the G1 phase. Human RNase III was only translocated to and remained in the nucleoli during S phase suggesting that RNase III may serve one or more specific functions in nucleoli during S phase.

The present invention also provides antisense inhibitors of RNase III expression, which may be used, for example, therapeutically, prophylactically or as research reagents. The modulation of function of a target nucleic acid (in this case a nucleic acid encoding RNase III) by compounds which specifically hybridize to it is generally referred to as "antisense".

The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the target. In the context of the present invention, "modulation" means either an increase (stimulation) or a decrease (inhibition) in the expression of a gene. In the context of the present invention, inhibition is the preferred form of modulation of gene expression and mRNA is a preferred target. In some embodiments gene silencing is a preferred form of inhibition of gene expression and refers to a decrease in gene expression mediated by a double-stranded RNA polynucleotide, one strand of which is homologous to the RNA to be silenced.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of the target, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds, including primers, probes, siRNAs, other double stranded RNAs including RNAi or gene silencing agents, ribozymes, external guide sequence (EGS) oligonucleotides (oligozymes), and other short catalytic RNAs or catalytic oligonucleotides which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "polynucleotide", which includes oligonucleotides, refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In general, nucleic acids or polynucleotides (including oligonucleotides) may be described as "DNA-like" (i.e., having 2'-deoxy sugars and, generally, T rather than U bases) or "RNA-like" (i.e., having 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-form-like structure are "RNA-like".

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_n$O]$_m CH_3$, O$(CH_2)_n OCH_3$, O$(CH_2)_n NH_2$, O$(CH_2)_n CH_3$, O$(CH_2)_n ONH_2$, and O$(CH_2)_n ON[(CH_2)_n CH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a O$(CH_2)_2$ON$(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—N$(CH_2)_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 3' or 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one).

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., Ann. N.Y. Acad. Sci., 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention preferably includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

By way of example, RNase H cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Oligonucleotides, particularly chimeric oligonucleotides, designed to elicit target cleavage by RNase H, thus are generally more potent than oligonucleotides of the same base sequence which are not so optimized. Cleavage of the RNA target can be routinely detected by, for example, gel electrophoresis and, if necessary, associated nucleic acid hybridization techniques known in the art.

Chimeric oligonucleotides may have one or more modifications of the internucleoside (backbone) linkage, the sugar or the base. In a preferred embodiment, the oligonucleotide is a chimeric oligonucleotide having a modification at the 2' position of at least one sugar moiety. Presently believed to be particularly preferred are chimeric oligonucleotides which have approximately four or more deoxynucleotides in a row, which provide an RNase H cleavage site, flanked on one or both sides by a region of 2'-modified oligonucleotides.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense inhibition of human RNase III expression was used to further evaluate the role(s) of RNase III. To identify optimal sites in RNase III mRNA for antisense effects, 2'-O-methoxyethyl chimeric antisense oligonucleotides targeted to 10 sites in the mRNA were designed and screened for inhibition of RNase III. These are shown in Table 1. These chimeric or "gapped" oligonucleotides are designed to serve as substrates for RNase H when bound to RNA resulting in degradation of the target RNA and oligonucleotides of this type have been shown to be highly specific when used under the described conditions.

TABLE 1

Antisense inhibition of human RNase III

| ISIS # | Sequence (5'→ 3') | Target sites | % Inhib'n | SEQ ID NO: |
|---|---|---|---|---|
| 25690 | ATCCCTTTCTTCCGCATGTG | 3051-3070 | 79 | 8 |
| 25691 | GCCAAGGCGTGACATGATAT | 3085-4004 | 96 | 9 |
| 25692 | CGGATCATTAAAGAGCAAGC | 3442-3461 | 78 | 10 |
| 25693 | TATTCACCAAAGAGCTTCGC | 3776-3795 | 49 | 11 |
| 25694 | CAATCGTGGAAAGAAGCAGA | 3973-3992 | 50 | 12 |
| 25695 | GCTCCCATTTCCGCTTGCTG | 4197-4216 | 81 | 13 |
| 25696 | ATGCTCTCTTTCCCACCTCA | 4308-4327 | 70 | 14 |
| 25697 | AAATACTCCACACTTGCATG | 4378-4397 | 79 | 15 |
| 25698 | TGCACATTCACCAAAGTCAA | 4420-4439 | 44 | 16 |
| 25699 | AGTCTAGGGTCACAATCTGG | 4688-4707 | 31 | 17 |
| 27110 | TTCAGTTGTAGTGGTCCGAC | 3-mismatch of 25691 | N/D | 18 |

All oligonucleotides in Table 1 have phosphorothioate (P=S or PS) backbones and 2'-methoxyethoxy (2'MOE) "wings" flanking a 2'deoxy gap. 2'MOE nucleotides are shown in bold. All cytosines are 5-methyl cytosines (5meC). Target site refers to nucleotide numbers on the cloned RNase III cDNA (SEQ ID NO: 1) to which the oligonucleotide binds. Oligonucleotide concentration was 200 nM.

Table 1 shows that ISIS 25690, 25691, 25692, 25693, 25694, 25695, 25696 and 25697 (SEQ ID NO: 8, 9, 10, 11, 12, 13, 14 and 15) inhibited human RNase III expression by about 50% or more. These compounds are therefore preferred. The most effective agent was ISIS 25691 (SEQ ID NO: 9), targeted to nucleotides 3085-4004 in the coding region of the mRNA. This compound was selected for further studies.

Increasing concentrations of ISIS 25691 caused increasing loss of RNase III mRNA, with 300 nM resulting in loss of more than 90% of the RNase III mRNA. The mismatch control oligonucleotide, ISIS 27110 (SEQ ID NO: 18), at 300 nM had no effect on the RNase III mRNA level. ISIS 25691 at 300 nM suppressed RNase III mRNA levels in HeLa cells from 2 to 72 hours after a single treatment. After treatment with ISIS 25691 at 100, 150 or 200 nM for 24 hours, RNase III protein was reduced to 67%, 44% or 19% of control respectively. The level of RNase III protein was slightly reduced at 5 hours after treatment and reached a maximum reduction of about 70% at 18 hours.

Immunofluorescence staining showed that after treatment with ISIS 25691 (150 nM, 24 hours), RNase III was dramatically reduced or absent in the nucleus and nucleoli. After treatment of HeLa cells with ISIS 25691 at 300 nM for 18 hours, the morphology of HeLa cells changed from fusiform to oval. After 24 hours of treatment, approximately 5-10% of the cells detached from the plate and could be stained with trypan blue indicating cell death. The cells that remained attached to the solid substrate grew much more slowly than untreated cells and appeared unable to enter mitosis (data not shown). After 48 hours, 40-50% of the cells treated with 300 nM ISIS 25691 were dead. These results were highly reproducible and indicate that RNase III is required for HeLa cell survival. The control oligonucleotide had no effect at any time or at any concentration on cell morphology, RNase III mRNA or protein levels demonstrating the antisense effect was highly specific.

One function that has been attributed to RNase III in lower species is pre-ribosomal RNA (pre-rRNA) processing. Human pre-rRNA processing is thought to involve cleavage of 45S pre-rRNA into 30S and 32S fragments. The 32S RNA product of the cleavage of 45S pre-rRNA contains 5.8S rRNA, ITS2 and 28S rRNA. Cleavage of the 32S RNA results in 12S pre-rRNA and 28S rRNA products. The 12S pre-rRNA is further cleaved to 5.8S rRNA. Because ribosomes are made in the nucleolus, and the human RNase III protein appeared to be translocated to and from the nucleolus during the cell cycle, its potential role(s) in human pre-rRNA processing was evaluated. Two hybridization probes for human pre-rRNA were synthesized, 5'ETS-1 (5'-CAA GGC ACG CCT CTC AGA TCG CTA GAG AAG GCT TTT CTC A-3'; SEQ ID NO: 19), designed to bind to the 5' external transcribed spacer (5'ETS) of human pre-rRNA and 5.8S-1 (5'-CAT TAA TTC TCG CAG CTA GCG CTG CGT TCT TCA TCG ACG C-3'; SEQ ID NO: 20), designed to bind to 5.8S rRNA. When total cellular RNA (15 µg) from untreated HeLa cells was fractionated by agarose gel electrophoresis, transferred to a nylon membrane and probed with $^{32}$P-5'ETS-1, a band corresponding to 45S pre-rRNA and a very faint band corresponding in mobility to 30S (5'ETS-18S-ITS1) pre-rRNA were observed. When $^{32}$P-5.8S-1 was used, bands corresponding to 45S, 32S (5.8S-ITS2-28S) and 12S (5.8S-ITS2) pre-rRNA and 5.8S rRNA were observed. At concentrations at which the antisense oligonucleotide ISIS 25691 dramatically reduced the RNase III level, no effect on the 45S pre-rRNA level was observed. In contrast, the 5.8S-1 probe demonstrated that antisense inhibition of RNase III increased the levels of 32S and 12S pre-rRNAs.

To provide further confirmation that human RNase III is involved in preribosomal RNA processing, the effects of ten antisense oligonucleotides on RNase III mRNA levels were compared to the effects of these oligonucleotides on accumulation of the two pre-rRNA species (32S and 12S) that accumulated after treatment with the most potent of the antisense inhibitors, ISIS 25691. The potency of antisense inhibitors designed to bind to different sites in RNase III mRNA varied. The correlation between the reduction of RNase III RNA levels and the accumulation of both 32S and 12S pre-rRNAs was excellent, thus confirming the conclusion derived from the Northern blot analysis.

Antisense inhibition of RNase III resulted in substantial accumulation of 12S pre-rRNA, less pronounced accumulation of 32S pre-rRNA and no accumulation of 45S pre-rRNA. Thus this human RNase III appears to be required for the processing of 12S pre-rRNA. It may also be involved in the processing of 32S pre-rRNA. The principal site of cleavage induced by human RNase III described here is in the 5.8S-ITS2 region of pre-rRNA.

RNase III enzymes are double-strand RNA (dsRNA) endoribonucleases. To test whether the human RNase III domain can specifically cleave dsRNA, the RNase III domain-coding region was subcloned into a glutathione S-transferase (GST) expression vector. The GST-RNase III fusion protein and GST alone were expressed, purified using glutathione agarose and analyzed by coomassie blue staining of the SDS-PAGE and Western Blot analysis with anti-human RNase III peptide antibody. These studies showed that the human RNase III domain was greater than 85% pure, though there was evidence of slight degradation during expression and purification. When incubated with labeled dsRNA and ssRNA, the GST-RNase III fusion protein preferentially digested the dsRNA without significant cleavage of ssRNA, while GST alone cleaved neither dsRNA nor ssDNA substrate. Thus, the cleavage observed was not due to contamination with ssRNases or dsRNases from *E. coli*. Ribonucleases $V_1$ (dsRNase), and $T_1$ and A (ssRNases) were used as controls to confirm that the cleavage observed was dsRNA cleavage.

RNase III is a double-strand RNA endonuclease, specifically cleaving double-helical structures in cellular and viral RNAs. It is believed that this cleavage can be exploited to promote cleavage of a cellular RNA target, by providing "RNA-like" antisense oligonucleotides which hybridize to the cellular RNA target to form an RNA duplex, thus eliciting RNase III cleavage. Methods of promoting inhibition of expression by antisense oligonucleotides, and methods for screening oligonucleotides are thus provided. In the context of this invention, "promoting antisense inhibition" or "promoting inhibition of expression" of a selected RNA target, or of its protein product, means inhibiting expression of the target or enhancing the inhibition of expression of the target. In some embodiments of these methods, the RNase III is present in an enriched amount. In the context of this invention, "enriched" means an amount greater than would naturally be found. RNase III may be present in an enriched amount through, for example, addition of exogenous RNase III, through selection of cells which overexpress RNase III or through manipulation of cells to cause overexpression of RNase III. The exogenously added RNase III may be added in the form of, for example, a cellular or tissue extract, a biochemically purified or partially purified preparation of RNase III, or a cloned and expressed RNase III polypeptide.

The expression of large quantities of a cloned human RNase III of the present invention has been shown to be useful in characterizing the activities of this enzyme. In addition, the polynucleotides and polypeptides of the present invention provide a means for identifying agents, such as the antisense compounds described herein, which modulate the function of this enzyme in human cells and tissues. For example, a host cell can be genetically engineered to incorporate polynucleotides and express polypeptides of the present invention. Polynucleotides can be introduced into a host cell using any number of well known techniques such as infection, transduction, transfection or transformation. The polynucleotide can be introduced alone or in conjunction with a second polynucleotide encoding a selectable marker. In a preferred embodiment, the host comprises a mammalian cell. Such host cells can then be used not only for production of human RNase III, but also to identify agents which increase or decrease levels of expression or activity of human RNase III in the cell. In these assays, the host cell would be exposed to an agent suspected of altering levels of expression or activity of human RNase III in the cells. The level or activity of human RNase III in the cell would then be determined in the presence and absence of the agent. Assays to determine levels of protein in a cell are well known to those of skill in the art and include, but are not limited to, radioimmunoassays, competitive binding assays, Western blot analysis and enzyme linked immunosorbent assays (ELISAs). Methods of determining increased activity of the enzyme, and in particular increased cleavage of dsRNA substrate can be performed in accordance with the teachings of the examples of the present application. Agents identified as modulators of the level or activity of this enzyme may be useful.

Antisense modulators of human RNase III are provided herein and may be used diagnostically, therapeutically and for research purposes.

The following nonlimiting examples are provided to further illustrate the present invention.

EXAMPLES

Example 1 cDNA Cloning

An internet search of the XREF database in the National Center of Biotechnology Information (NCBI) yielded a 393 base pair (bp) human expressed sequenced tag (EST, GenBank accession AA083888), homologous to the yeast RNase III (RNT1) gene (GenBank accession #AAB04172; SEQ ID NO: 5) and the *C. elegans* RNase III gene (GenBank accession 001326; SEQ ID NO: 3). Three sets of oligonucleotide primers encoding the human RNase H EST sequence were synthesized. Sequence-specific primer sets listed in Table 2 were designed based on the human expressed tag sequence or early cloned cDNA fragments. These are shown in Table 2. These primers were used in polymerase chain reaction for 3' and 5' RACE and/or for detection on Southern blots.

TABLE 2

RNase III Oligonucleotide Primers

| Primer name | Sequence source | Position in full length cDNA | SEQ ID NO | Primer Sequence |
|---|---|---|---|---|
| NIII-2 | EST AA083888 | 3516-3550 | 21 | CCAAATACTGATCGACAACTTATTGAAACTTCTCC |
| NIII-4 | EST AA083888 | 3569-3606 | 22 | GAGTTTGAAGAAGCAATTGGAGTAATTTTTACTCATG |
| NIII-6 | EST AA083888 | 3607-3634 | 23 | TCGACTTCTGGCAAGGGCATTCACATT |
| 3RACE3 | Clone #3-4 | 2708-2683 | 24 | CCTCTGTGCCAGCTTCTGTTTGTCAG |
| 3RACE2 | Clone #3-4 | 2688-2663 | 25 | TGTCAGTTTGTTTGACTTTGGGACTA |
| 3RACE1 | Clone #3-4 | 2662-2637 | 26 | TTTGCTAGGAGGTGGCGAAGTTTCAC |
| RACE4 | Clone #L40 | 1923-1894 | 27 | GCTTGATGGCCTCTTCTCCAGGATAAATGC |
| RACE5 | Clone #L40 | 1898-1869 | 28 | AATGCTGTGCCTAATTCCTGTGCGTCTTGC |
| RACE Det | Clone #L40 | 1723-1676 | 29 | CAGGTGCTGTCCTCATCAGACTCACACTCGGATTCACTGGAACTCTCT |

TABLE 2-continued

RNase III Oligonucleotide Primers

| Primer name | Sequence source | Position in full length cDNA | SEQ ID NO | Primer Sequence |
|---|---|---|---|---|
| 33G | Clone #25 | 831-806 | 30 | CACTGGGCAGGAAAGAACTAGGGTTG |
| 33H | Clone #25 | 802-776 | 31 | TGGAAACTATTAAAACTGGGAGGTGG |
| 33 Det | Clone #25 | 701-652 | 32 | AGGCATGGAGGGAGGGGCATCATGAAGG GGAAAGTGCCTTGTCCAGGAG |

By 3' RACE (rapid amplification of 3' cDNA), the human RNase III cDNA 3' from the expressed tag sequence was amplified by PCR using human Marathon ready cDNA (Clontech, Palo Alto Calif.) as templates, and NIII-2/AP1 (for the first amplification) and NIII-4/AP2 (for the second amplification) as primers. AP1 and AP2 are primers provided with the Marathon ready cDNA by the manufacturer. The standard DNA polymerase chain reaction (PCR) procedure was performed using native pfu DNA polymerase (Stratagene, San Diego Calif.) and its reaction buffer. The annealing temperature was 55-60° C. The elongation time was approximately 6-8 min. The fragments were subjected to agarose gel electrophoresis. The fragments were subjected to agarose gel electrophoresis in the TAE buffer, denatured in 0.5 M NaOH and then electronically transferred to a nitrocellulose membrane (Bio-Rad, Hercules, Calif.) for confirmation by Southern blot. Southern blots were performed using [$^{32}$P]-end labeled NIII-6 oligonucleotide as a probe in hybridization buffer (6× SSC, 5× Denhardts solution) containing 100 μg/ml sheared denatured salmon sperm DNA, 0.5% SDS, 10 mM EDTA at 46° C. for 4 hr, then washed twice with 1× SSC and 0.1% SDS at 42-59° C. for 20 min. The confirmed fragments were excised from the agarose gel and purified by gel extraction (Qiagen, Germany), then subcloned into a zero-blunt vector (Invitrogen, Carlsbad, Calif.) and subjected to DNA sequencing.

Example 2

Screening of the cDNA Libraries, DNA Sequencing and Sequence Analysis

A human liver cDNA lambda phage Uni-ZAP library (Stratagene, La Jolla, Calif.) was screened using the RACE products as specific probes. Several positive clones were isolated. The two longest clones, 3-1 and 3-4, correspond to the COOH-terminal region, nucleotides 2636-3912 and 3350-4764, respectively, of the full length cDNA. With primers (3RACE1, 3RACE2 and 3RACE3) based on the NH$_2$-terminal portion of the clone 3-4, 5' RACE was performed to clone a cDNA (clone L40) of approximately 1 kb, which encodes the middle part (nucleotides 1661-2688) of the full length cDNA. In the same way, a cDNA (clone 25) of the NH$_2$-terminal portion (nucleotides 645-1898) was cloned. Using clone 25 to screen the liver library again, several clones were isolated, but none included additional NH$_2$-terminal sequence. The most NH$_2$-terminal clone (328) corresponded to nucleotides 799-2191. The last 5' RACE was performed with primers 33G, 33H and 33Dec, based on clone 25, and the NH$_2$-terminal portion of the cDNA (clone 81, corresponding to nucleotides 1-802) was generated.

The positive cDNA clones were excised into pBluescript phagemid from lambda phage and subjected to DNA sequencing. Sequencing of the positive clones was performed with an automatic DNA sequencer by Retrogen Inc. (San Diego, Calif.). The overlapping sequences were aligned and combined by the assembling program of MacDNASISv3.0 (Hitachi Software Engineering Co., America, Ltd.) to give the full length (4764 nucleotides) polynucleotide sequence (SEQ ID NO: 1). Protein structure and analysis were performed by the program MacVector v6.0 (Oxford Molecular Group, UK). A homology search was performed on the NCBI database.

Example 3

Antisense Treatment

HeLa cells were transfected with oligonucleotide mixed with Lipofectin (GIBCO BRL, Gaithersburg, Md.) at a concentration of 37.5-300 nM for 5 hours in Opti-MEM (GIBCO BRL). After removing the medium containing oligonucleotide, cells were cultured in DMEM for times indicated and harvested for analysis. Inhibition by antisense oligonucleotides is expressed compared to control (without oligonucleotide treatment).

Example 4

Northern Hybridization

Total RNA was isolated from HeLa cells using the guanidine isothiocyanate method (R. E. Kingston, in *Current protocols in molecular biology*, F. M. Ausubel, et al., Eds., John Wiley & Sons Inc., New York, 1997, vol. 1, pp. 4.2.3-4.2.5.). Fifteen μg of total RNA was separated on a 1% agarose/formaldehyde gel and transferred to Hybond-N+ (Amersham, Arlington Heights, Ill.) followed by fixing using UV crosslinker (Stratagene, La Jolla, Calif.). To detect RNase III mRNA, hybridization was performed by using $^{32}$P-labeled human RNase III cDNA in Quik-Hyb buffer (Stratagene, La Jolla, Calif.) at 68° C. for 2 hours. After hybridization, membranes were washed in a final stringency of 0.1× SSC/0.1% SDS at 60° C. for 30 minutes. Membranes were analyzed using a Phosphorlmager Storm 860 (Molecular Dynamics, Sunnyvale, Calif.). The level of glyceraldehyde-3-phosphate dehydrogenase (GAPDH) mRNA was used to normalize the amount of total RNA loaded.

For Northern hybridization of pre-rRNAs, HeLa cells were treated with ISIS 25691 and ISIS 27110 for 24 hours using $^{32}$P-end labeled oligo probes 5'ETS-1 (5'-CAA GGC ACG CCT CTC AGA TCG CTA GAG AAG GCT TTT CTC A-3'; SEQ ID NO: 33), corresponding to 5'ETS and 5.8S-1(5'-CAT TAA TTC TCG CAG CTA GCG CTG CGT TCT TCA TCG ACG C-3'; SEQ ID NO: 34), corresponding to 5.8S rRNA. Hybridizations were performed at 40° C. for 2 hours and washed in 2×SSC/0.1%SDS at 40° C. for 1 hour. All others were as described above. Data were mean±SD of triplicate determination of representative experiment.

Example 5

Western Blot Analysis of Human RNase III

Nuclear and non-nuclear fractions from HeLa cells were prepared as described (Dignam et al., *Nucleic Acids Res* 1983, 11, 1475-89. Whole cell, non-nuclear and nuclear fractions were boiled in SDS-sample buffer. Then the samples were separated by SDS-PAGE using 4-20% Tris-glycine gels (NOVEX, San Diego, Calif.) under reducing conditions. Molecular weight prestained markers were used (NOVEX) to determine the protein sizes. The proteins were electrophoretically transferred to a PVDF-membrane and processed for immunoblotting using affinity purified anti-SR peptide antibody at 5 µg/ml. The immunoreactive bands were visualized using the enhanced chemiluminescence method (Amersham, Arlington Heights, Ill.) and analyzed using a PhosphorImager Storm 860 (Molecular Dynamics, Sunnyvale, Calif.).

Example 6

Antibody Production

Antibodies were prepared to peptides synthesized having amino acid sequences contained within the SR domain and the III domain of human RNase III. The SR domain peptide (H-CRSDYDRGRTPSRHRSYERS-OH, amino acids 226 to 284; SEQ ID NO: 35) and the III region peptide (H-CRWEREHQEREPDETEDIKK-OH, amino acids 1356 to 1374; SEQ ID NO: 36) were synthesized, coupled to diphtheria toxoid through maleimidocaproyl-N-hydroxysuccinamide (MCS), mixed with Freund's adjuvant (complete for first immunization, incomplete for remaining immunizations) and injected intramuscularly into New Zealand White rabbits. Serum was collected after the second immunization. Antibody titer was measured by ELISA. Anti-SR and anti-III peptide IgGs were affinity purified with SR and III peptides coupled to thiopropyl-Sepharose 6B, respectively.

Example 7

Indirect Immunofluorescence Staining of Human RNase III

HeLa cells were cultured in chamber slides for immunostaining. Cells were washed once with Dulbecco's Phosphate Buffered Saline (D-PBS, pH7.0), and then fixed in 10% neutral-buffered formalin for 10 minutes followed by washing three times with D-PBS. Fixed cells were then blocked for 30 minutes with 20% fetal bovine serum plus 0.5% Tween 20. Cells were first stained with anti-III peptide antibody (10 µg/ml) for 1 hour at 37° C., washed three times with D-PBS plus 0.1% NP-40, and incubated for 1 hour at 37° C. with the FITC goat anti-rabbit IgG (Jackson ImmunoResearch Laboratory, Inc. West Grove, Pa.). The cells were washed with D-PBS three times and mounted in mounting medium (Vector, Burlingame, Calif.) for examination under a fluorescence microscope. NR IgG: normal rabbit IgG was used as control.

Example 8

Indirect Immunofluorescence Staining of Human RNase III in HeLa Cells in Different Phases of the Cell Cycle HeLa cells were synchronized at early-S phase using the double thymidine method (Johnson et al., in *The Cell Cycle: A Practical Approach* P. Fantes, R. Brooks, Eds., IRL Press, 1993, pp. 1-24). Briefly, cells were cultured in Dulbecco's Modified Eagle Medium (DMEM, 10% fetal calf serum) containing 2 mM of thymidine for 17 hours. After washing twice with D-PBS, cells were cultured in DMEM for 9 hours followed by second thymidine treatment for 15 hours. Synchronized cells were then washed twice with D-PBS, cultured and harvested at 0, 2, 4, 6, 8 and 24 hours for immunofluorescence staining and FACS analysis. HeLa cells were detached from culture flasks with trypsin-EDTA and washed once with D-PBS containing 5 mM of EDTA. Cells were then fixed in 70% ethanol for 1 to 24 hours at 4° C. followed by propidium iodine (PI, 50 µg/ml) staining for 1 hour at room temperature. Cell counts (Y axis) and PI content (X axis) were determined by FACS analysis (Becton Dickinson and Co., San Jose, Calif.).

Example 9

Expression of GST-RNase III Domain Fusion Protein

A cDNA fragment encoding the human RNase III-like domain (C-terminal-most 466 amino acids) was amplified by PCR and introduced into a BamH I site upstream and Not I site downstream. This fragment was further subcloned into the sites of the expression vector pGEX-4T-1 (Pharmacia Biotech, Piscataway, N.J.) to produce the RNase III fusion protein with Glutathione S-transferase (GST) at its N-terminus. The identity of the construct was proven by DNA sequencing. The GST-RNase III fusion protein was expressed in *E. coli* strain BL21 and purified using glutathione agarose (Pharmacia Biotech, Piscataway, N.J.) under native conditions with B-PER bacterial protein extraction reagent (Pierce, Rockford, Ill.). Control GST protein was also prepared in parallel from the pGEX-4T-1 plasmid. The purified products were identified by Coomassie staining after 12% SDS-polyacrylamide gel electrophoresis and Western blot analyses with anti-RNase III peptide antibody (see examples above).

Example 10

In Vitro Cleavage of dsRNA

The dsRNA substrate was generated by hybridization of two complementary strands of RNA produced with T7 and T3 polymerase transcription of the polylinker region of the pBluscript II KS(−) plasmid (Stratagen, San Diego, Calif.). The plasmid was digested with either Sst I or Kpn I and further purified with phenol/chloroform extraction and ethanol precipitation. The Sst I or Kpn I-digested plasmids were then transcribed using T7 or T3 RNA polymerase respectively (Stratagene, San Diego, Calif.) with or without $^{32}$P-αUTP. The resulting transcribed RNAs (about 100 nt) were purified by electrophoresis on 6% denaturing polyacrylamide gel. The $^{32}$P radiolabeled T7 transcript and unlabeled T3 transcript fragments were mixed and heated for 5 min at 90° C. in a buffer containing 20 mM KCl, 50 mM Tris-HCl (pH 7.5), 0.1 mM EDTA. MgCl, BSA and RNase inhibitor were added to the mixture after heating (final concentrations were 10 mM.

100 ng/ml and 10 unit/ml respectively). The mixture was incubated at 37° C. for 2 hr and the duplex RNA was purified on 6% non-denaturing gels. The $^{32}$P-labelled T7 transcript was also used as the ssRNA control substrate. To evaluate cleavage, 0.4 μg of GST protein or GST-RNase III (approximately 5-10 pmole of purified GST-RNase III) fusion protein was incubated with labeled dsRNA (250,000 cpm) (approximately 5-10 fmole) and ssRNA (250,000 cpm) at 37° C. in a buffer containing 20 mM KCl, 50 mM Tris-HCl (pH 7.5), 5 mM MgCl, 50 mM NaCl, 0.1 mM DTT, 0.1 mg/ml yeast tRNA and 10 unit/ml RNase inhibitor in the total volume of 60 μl. The digested samples were quenched at specific times and analyzed using non-denaturing polyacrylamide gel electrophoresis and PhosphorImager analysis.

What is claimed is:

1. A method of increasing cleavage of a target RNA in a mammalian cell comprising increasing the amount of a polypeptide in the cell, wherein the polypeptide comprises amino acids 906-1374 of the amino acid sequence recited as SEQ ID NO: 2 and wherein the RNA target comprises a double helical structure; and thereby increasing cleavage of the target RNA in the mammalian cell.

2. The method of claim 1, wherein the increasing the amount of the polypeptide comprises overexpression of the polypeptide.

3. The method of claim 1, wherein the polypeptide consists of the amino acid sequence recited as SEQ ID NO: 2.

4. The method of claim 1, wherein the cell is a human cell.

5. The method of claim 4, wherein the increasing the amount of the polypeptide comprises overexpression of the polypeptide.

6. The method of claim 4, wherein the polypeptide consists of the amino acid sequence of SEQ ID NO: 2.

* * * * *

```
                           SEQUENCE LISTING

<160> NUMBER OF SEQ ID NOS: 36

<210> SEQ ID NO 1
<211> LENGTH: 4764
<212> TYPE: DNA
<213> ORGANISM: Homo sapiens

<400> SEQUENCE: 1
ctgtcttggt acctgcggta gtagcctggc tttgctctga cggcgatctc gcggcccgag     60
agccttttat aggttgcttt tcccggggat gtgaaggata cagaaatgac tgtgaatcaa    120
cccatatcat caaggagctg ataatctagt ggaagagtta gacgtgtgca tacttcacta    180
tgatatgagg cagtctctga gcttatattc tctgtggaag atgtgacata tccaggcgga    240
acatcatgat gcagggaaac acatgtcaca gaatgtcgtt ccacccggga cgagggcgtc    300
cccgaggacg aggaggacat ggagccagac cctcagcacc atcctttagg ccccaaaatc    360
tgaggctgct tcaccctcag cagcctcctg tgcaatatca atatgaacct ccaagtgccc    420
cttccaccac tttctcaaac tctccagccc ccaattttct ccctccacga ccagactttg    480 taccttccc cccacccatg cctccgtcag cgcaaggccc tcttccccc tgcccaatca    540 ggccgccttt ccccaaccac cagatgaggc accccttccc agttcctcct tgttttcctc    600
ccatgccacc accaatgcct tgtcctaata acccccagt ccctggggca cctcctggac    660
aaggcacttt cccccttcatg atgcccccctc cctccatgcc tcatcccccg cccctccag    720 tcatgccgca gcaggttaat tatcagtacc ctccgggcta ttctcaccac aacttcccac    780
ctcccagttt taatagtttc cagaacaacc ctagttcttt cctgcccagt gctaataaca    840
gcagtagtcc tcatttcaga catctccctc catacccact cccaaaggct cccagtgaga    900
gaaggtcccc agaaaggctg aaacactatg atgaccacag gcaccgagac cacagtcatg    960
ggcgaggtga gaggcatcgg tccctggatc ggcgggagcg aggccgcagt cccgacagga   1020
gaagacaaga cagccggtac agatctgatt atgaccgagg gagaacacca tctcgccacc   1080
gcagctacga acggagcaga gagcgagaac gggagagaca caggcatcga gacaaccgaa   1140
gatcaccatc tctggaaagg tcctacaaaa aagagtataa gagatctgga aggagttacg   1200
gtttatcggt tgttcctgaa cctgctggat gcacaccaga attacctggg gagattatta   1260
aaaatacaga ttcttgggcc ccacccctgg agattgtgaa tcatcgctcc caagtaggg   1320 agaagaagag agctcgttgg gaggaagaaa aagaccgttg gagtgacaac cagagttctg   1380
gcaaagacaa gaactatacc tcaatcaagg aaaaagagcc cgaggagacc atgcctgaca   1440
```

-continued

```
agaatgagga ggaagaagaa gaacttctta agcctgtgtg gattcgatgc actcattcag   1500
aaaactacta ctccagtgac cccatggatc aggtgggaga ttctacagtg gttggaacga   1560
gtaggcttcg tgacttatat gacaaatttg aggaggagtt ggggagcagg caagaaaagg   1620
ccaaagctgc tcggcctccg tgggaacctc caaagacgaa gctcgatgaa gatttagaga   1680
gttccagtga atccgagtgt gagtctgatg aggacagcac ctgttctagc agctcagact   1740
ctgaagtttt tgacgttatt gcagaaatca aacgcaaaaa ggcccaccct gaccgacttc   1800
atgatgaact ttggtacaac gatccaggcc agatgaatga tggaccactc tgcaaatgca   1860
gcgcaaaggc aagacgcaca ggaattaggc acagcattta tcctggagaa gaggccatca   1920
agccctgtcg tcctatgacc aacaatgctg cagacttttt ccactaccgg atcacagtct   1980
ccccgcctac gaactttta actgacaggc caactgttat agaatacgat gatcacgagt   2040
atatctttga aggattttct atgtttgcac atgccccct gaccaatatt ccactgtgta   2100
aagtaattag attcaacata gactacacga ttcatttcat tgaagagatg atgccggaga   2160
attttgtgt gaaagggctt gaactctttt cactgttcct attcagagat attttgaat   2220
tatatgactg gaatcttaaa ggtccttgt ttgaagacag ccctccctgc tgcccaagat   2280
ttcatttcat gccacgtttt gtaagatttc ttccagatgg aggaaaggaa gtgctgtcca   2340
tgcaccagat tctcctgtac ttgttaaggt gcagcaaagc cctggtgcct gaggaggaga   2400
ttgccaatat gcttcagtgg gaggagctgg agtggcagaa atatgcagaa gaatgcaaag   2460
gcatgattgt taccaacccct gggacgaaac caagctctgt ccgtatcgat caactggatc   2520
gtgaacagtt caaccccgat gtgattactt ttccgattat cgtccacttt gggatacgcc   2580
ctgcacagtt gagttatgca ggagacccac agtaccaaaa actgtggaag agttatgtga   2640
aacttcgcca cctcctagca aatagtccca aagtcaaaca aactgacaaa cagaagctgg   2700
cacagaggga ggaagccctc caaaaaatac ggcagaagaa tacaatgaga cgagaagtaa   2760
cggtggagct aagtagccaa ggattctgga aaactggcat ccgttctgat gtctgtcagc   2820
atgcaatgat gctacctgtt ctgacccatc atatccgcta ccaccaatgc taatgcatt   2880
tggacaagtt gataggatat acttccaag atcgttgtct gttgcagctg ccatgactc   2940
atccaagtca tcatttaaat tttgaatga atcctgatca tgccaggaat tcattatcta   3000
actgtggaat tcggcagccc aaatacggag acagaaaagt tcatcacatg cacatgcgga   3060
agaaagggat taacaccttg ataaatatca tgtcacgcct tggccaagat gacccaactc   3120
cctcgaggat taaccacaat gaacggttgg aattcctggg tgatgctgtt gttgaatttc   3180
tgaccagcgt ccatttgtac tatttgtttc ctagtctgga agaaggagga ttagcaacct   3240
atcggactgc cattgttcag aatcagcacc ttgccatgct agcaaagaaa cttgaactgg   3300
atccatttat gctgtatgct cacgggcctg acctttgtag agaatcggac cttcgacatg   3360
caatggccaa ttgttttgaa gcgttaatag gagctgttta cttggaggga agcctggagg   3420
aagccaagca gttatttgga cgcttgctct ttaatgatcc ggacctgcgc gaagtctggc   3480
tcaattatcc tctccaccca ctccaactac aagagccaaa tactgatcga caacttattg   3540
aaacttctcc agttctacaa aaacttactg agtttgaaga agcaattgga gtaattttta   3600
ctcatgttcg acttctggca agggcattca cattgagaac tgtgggattt aaccatctga   3660
ccctaggcca caatcagaga atggaattcc taggtgactc cataatgcaa ctggtagcca   3720
cagagtactt attcattcat ttcccagatc atcatgaagg acacttaact ttgttgcgaa   3780
```

-continued

```
gctctttggt gaataataga actcaggcca aggtagcgga ggagctgggc atgcaggagt    3840
acgccataac caacgacaag accaagaggc ctgtggcgct tcgcaccaag accttggcgg    3900
accttttgga atcatttatt gcagcgctgt acactgataa ggatttggaa tatgttcata    3960
ctttcatgaa tgtctgcttc tttccacgat tgaaagaatt cattttgaat caggattgga    4020
atgaccccaa atcccagctt cagcagtgtt gcttgacact taggacagaa ggaaaagagc    4080
cagacattcc tctgtacaag actctgcaga cagtgggccc atcccatgcc cgaacctaca    4140
ctgtggctgt ttatttcaag ggagaaagaa taggctgtgg aaaggacca agtattcagc     4200
aagcggaaat gggagcagca atggatgcgc ttgaaaaata taattttccc cagatggccc    4260
atcagaagcg gttcatcgaa cggaagtaca gacaagagtt aaaagaaatg aggtgggaaa    4320
gagagcatca agagagagag ccagatgaga ctgaagacat caagaaataa aggagggcat    4380
gcaagtgtgg agtatttact tgctcagtaa ctgtgactgt tgtctattga gacctagcct    4440
agttttcctg cagacaatga acgaagtgtg ctcattgaaa taaatacag agtcaaatcg     4500
ctattgttgt tttaatgatc tgttttttagc tggatggtct ttattacaaa gtattagatt    4560
tttcttctat ttaacggaaa acttgacttt ggtgaatgtg cattacttcc ttttatttttg   4620
ctctttaaat aataaaattc aagaagcata ttctatgtgg aatagatcct gttttttccat    4680
ctgtgtccca gattgtgacc ctagactttc aattgacaag taaaaaattg actttactag    4740
taaaaaaaaa aaaaaaaaaa aaaa                                            4764
```

<210> SEQ ID NO 2
<211> LENGTH: 1374
<212> TYPE: PRT
<213> ORGANISM: Homo sapiens

<400> SEQUENCE: 2

```
Met Met Gln Gly Asn Thr Cys His Arg Met Ser Phe His Pro Gly Arg
1               5                   10                  15

Gly Cys Pro Arg Gly Arg Gly Gly His Gly Ala Arg Pro Ser Ala Pro
            20                  25                  30

Ser Phe Arg Pro Gln Asn Leu Arg Leu Leu His Pro Gln Gln Pro Pro
        35                  40                  45

Val Gln Tyr Gln Tyr Glu Pro Pro Ser Ala Pro Ser Thr Thr Phe Ser
    50                  55                  60

Asn Ser Pro Ala Pro Asn Phe Leu Pro Pro Arg Pro Asp Phe Val Pro
65                  70                  75                  80

Phe Pro Pro Pro Met Pro Pro Ser Ala Gln Gly Pro Leu Pro Pro Cys
                85                  90                  95

Pro Ile Arg Pro Pro Phe Pro Asn His Gln Met Arg His Pro Phe Pro
            100                 105                 110

Val Pro Pro Cys Phe Pro Pro Met Pro Pro Met Pro Cys Pro Asn
        115                 120                 125

Asn Pro Pro Val Pro Gly Ala Pro Gly Gln Gly Thr Phe Pro Phe
    130                 135                 140

Met Met Pro Pro Pro Ser Met Pro His Pro Pro Pro Pro Val Met
145                 150                 155                 160

Pro Gln Gln Val Asn Tyr Gln Tyr Pro Pro Gly Tyr Ser His His Asn
                165                 170                 175

Phe Pro Pro Pro Ser Phe Asn Ser Phe Gln Asn Asn Pro Ser Ser Phe
            180                 185                 190

Leu Pro Ser Ala Asn Asn Ser Ser Ser Pro His Phe Arg His Leu Pro
```

-continued

```
                195                 200                 205
Pro Tyr Pro Leu Pro Lys Ala Pro Ser Glu Arg Ser Pro Glu Arg
    210                 215                 220

Leu Lys His Tyr Asp Asp His Arg His Arg Asp His Ser His Gly Arg
225                 230                 235                 240

Gly Glu Arg His Arg Ser Leu Asp Arg Arg Glu Arg Gly Arg Ser Pro
                245                 250                 255

Asp Arg Arg Arg Gln Asp Ser Arg Tyr Arg Ser Asp Tyr Asp Arg Gly
                260                 265                 270

Arg Thr Pro Ser Arg His Arg Ser Tyr Glu Arg Ser Arg Glu Arg Glu
                275                 280                 285

Arg Glu Arg His Arg His Arg Asp Asn Arg Arg Ser Pro Ser Leu Glu
                290                 295                 300

Arg Ser Tyr Lys Lys Glu Tyr Lys Arg Ser Gly Arg Ser Tyr Gly Leu
305                 310                 315                 320

Ser Val Val Pro Glu Pro Ala Gly Cys Thr Pro Glu Leu Pro Gly Glu
                325                 330                 335

Ile Ile Lys Asn Thr Asp Ser Trp Ala Pro Pro Leu Glu Ile Val Asn
                340                 345                 350

His Arg Ser Pro Ser Arg Glu Lys Lys Arg Ala Arg Trp Glu Glu Glu
                355                 360                 365

Lys Asp Arg Trp Ser Asp Asn Gln Ser Ser Gly Lys Asp Lys Asn Tyr
                370                 375                 380

Thr Ser Ile Lys Glu Lys Glu Pro Glu Glu Thr Met Pro Asp Lys Asn
385                 390                 395                 400

Glu Glu Glu Glu Glu Glu Leu Leu Lys Pro Val Trp Ile Arg Cys Thr
                405                 410                 415

His Ser Glu Asn Tyr Tyr Ser Ser Asp Pro Met Asp Gln Val Gly Asp
                420                 425                 430

Ser Thr Val Val Gly Thr Ser Arg Leu Arg Asp Leu Tyr Asp Lys Phe
                435                 440                 445

Glu Glu Glu Leu Gly Ser Arg Gln Glu Lys Ala Lys Ala Ala Arg Pro
                450                 455                 460

Pro Trp Glu Pro Pro Lys Thr Lys Leu Asp Glu Asp Leu Glu Ser Ser
465                 470                 475                 480

Ser Glu Ser Glu Cys Glu Ser Asp Glu Asp Ser Thr Cys Ser Ser Ser
                485                 490                 495

Ser Asp Ser Glu Val Phe Asp Val Ile Ala Glu Ile Lys Arg Lys Lys
                500                 505                 510

Ala His Pro Asp Arg Leu His Asp Glu Leu Trp Tyr Asn Asp Pro Gly
                515                 520                 525

Gln Met Asn Asp Gly Pro Leu Cys Lys Cys Ser Ala Lys Ala Arg Arg
                530                 535                 540

Thr Gly Ile Arg His Ser Ile Tyr Pro Gly Glu Glu Ala Ile Lys Pro
545                 550                 555                 560

Cys Arg Pro Met Thr Asn Asn Ala Gly Arg Leu Phe His Tyr Arg Ile
                565                 570                 575

Thr Val Ser Pro Pro Thr Asn Phe Leu Thr Asp Arg Pro Thr Val Ile
                580                 585                 590

Glu Tyr Asp Asp His Glu Tyr Ile Phe Glu Gly Phe Ser Met Phe Ala
                595                 600                 605

His Ala Pro Leu Thr Asn Ile Pro Leu Cys Lys Val Ile Arg Phe Asn
                610                 615                 620
```

-continued

```
Ile Asp Tyr Thr Ile His Phe Ile Glu Glu Met Met Pro Glu Asn Phe
625                 630                 635                 640

Cys Val Lys Gly Leu Glu Leu Phe Ser Leu Phe Leu Phe Arg Asp Ile
                645                 650                 655

Leu Glu Leu Tyr Asp Trp Asn Leu Lys Gly Pro Leu Phe Glu Asp Ser
                660                 665                 670

Pro Pro Cys Cys Pro Arg Phe His Phe Met Pro Arg Phe Val Arg Phe
                675                 680                 685

Leu Pro Asp Gly Gly Lys Glu Val Leu Ser Met His Gln Ile Leu Leu
690                 695                 700

Tyr Leu Leu Arg Cys Ser Lys Ala Leu Val Pro Glu Glu Glu Ile Ala
705                 710                 715                 720

Asn Met Leu Gln Trp Glu Glu Leu Glu Trp Gln Lys Tyr Ala Glu Glu
                725                 730                 735

Cys Lys Gly Met Ile Val Thr Asn Pro Gly Thr Lys Pro Ser Ser Val
                740                 745                 750

Arg Ile Asp Gln Leu Asp Arg Glu Gln Phe Asn Pro Asp Val Ile Thr
                755                 760                 765

Phe Pro Ile Ile Val His Phe Gly Ile Arg Pro Ala Gln Leu Ser Tyr
770                 775                 780

Ala Gly Asp Pro Gln Tyr Gln Lys Leu Trp Lys Ser Tyr Val Lys Leu
785                 790                 795                 800

Arg His Leu Leu Ala Asn Ser Pro Lys Val Lys Gln Thr Asp Lys Gln
                805                 810                 815

Lys Leu Ala Gln Arg Glu Glu Ala Leu Gln Lys Ile Arg Gln Lys Asn
                820                 825                 830

Thr Met Arg Arg Glu Val Thr Val Glu Leu Ser Ser Gln Gly Phe Trp
                835                 840                 845

Lys Thr Gly Ile Arg Ser Asp Val Cys Gln His Ala Met Met Leu Pro
850                 855                 860

Val Leu Thr His His Ile Arg Tyr His Gln Cys Leu Met His Leu Asp
865                 870                 875                 880

Lys Leu Ile Gly Tyr Thr Phe Gln Asp Arg Cys Leu Leu Gln Leu Ala
                885                 890                 895

Met Thr His Pro Ser His His Leu Asn Phe Gly Met Asn Pro Asp His
                900                 905                 910

Ala Arg Asn Ser Leu Ser Asn Cys Gly Ile Arg Gln Pro Lys Tyr Gly
                915                 920                 925

Asp Arg Lys Val His His Met His Met Arg Lys Lys Gly Ile Asn Thr
                930                 935                 940

Leu Ile Asn Ile Met Ser Arg Leu Gly Gln Asp Asp Pro Thr Pro Ser
945                 950                 955                 960

Arg Ile Asn His Asn Glu Arg Leu Glu Phe Leu Gly Asp Ala Val Val
                965                 970                 975

Glu Phe Leu Thr Ser Val His Leu Tyr Tyr Leu Phe Pro Ser Leu Glu
                980                 985                 990

Glu Gly Gly Leu Ala Thr Tyr Arg  Thr Ala Ile Val Gln  Asn Gln His
                995                 1000                1005

Leu Ala  Met Leu Ala Lys Lys  Leu Glu Leu Asp Pro  Phe Met Leu
     1010                1015                1020

Tyr Ala  His Gly Pro Asp Leu  Cys Arg Glu Ser Asp  Leu Arg His
     1025                1030                1035
```

```
Ala Met Ala Asn Cys Phe Glu Ala Leu Ile Gly Ala Val Tyr Leu
    1040                1045                1050

Glu Gly Ser Leu Glu Glu Ala Lys Gln Leu Phe Gly Arg Leu Leu
    1055                1060                1065

Phe Asn Asp Pro Asp Leu Arg Glu Val Trp Leu Asn Tyr Pro Leu
    1070                1075                1080

His Pro Leu Gln Leu Gln Glu Pro Asn Thr Asp Arg Gln Leu Ile
    1085                1090                1095

Glu Thr Ser Pro Val Leu Gln Lys Leu Thr Glu Phe Glu Glu Ala
    1100                1105                1110

Ile Gly Val Ile Phe Thr His Val Arg Leu Leu Ala Arg Ala Phe
    1115                1120                1125

Thr Leu Arg Thr Val Gly Phe Asn His Leu Thr Leu Gly His Asn
    1130                1135                1140

Gln Arg Met Glu Phe Leu Gly Asp Ser Ile Met Gln Leu Val Ala
    1145                1150                1155

Thr Glu Tyr Leu Phe Ile His Phe Pro Asp His His Glu Gly His
    1160                1165                1170

Leu Thr Leu Leu Arg Ser Ser Leu Val Asn Asn Arg Thr Gln Ala
    1175                1180                1185

Lys Val Ala Glu Glu Leu Gly Met Gln Glu Tyr Ala Ile Thr Asn
    1190                1195                1200

Asp Lys Thr Lys Arg Pro Val Gly Leu Arg Thr Lys Thr Leu Ala
    1205                1210                1215

Asp Leu Leu Glu Ser Phe Ile Ala Ala Leu Tyr Thr Asp Lys Asp
    1220                1225                1230

Leu Glu Tyr Val His Thr Phe Met Asn Val Cys Phe Phe Pro Arg
    1235                1240                1245

Leu Lys Glu Phe Ile Leu Asn Gln Asp Trp Asn Asp Pro Lys Ser
    1250                1255                1260

Gln Leu Gln Gln Cys Cys Leu Thr Leu Arg Thr Glu Gly Lys Glu
    1265                1270                1275

Pro Asp Ile Pro Leu Tyr Lys Thr Leu Gln Thr Val Gly Pro Ser
    1280                1285                1290

His Ala Arg Thr Tyr Thr Val Ala Val Tyr Phe Lys Gly Glu Arg
    1295                1300                1305

Ile Gly Cys Gly Lys Gly Pro Ser Ile Gln Gln Ala Glu Met Gly
    1310                1315                1320

Ala Ala Met Asp Ala Leu Glu Lys Tyr Asn Phe Pro Gln Met Ala
    1325                1330                1335

His Gln Lys Arg Phe Ile Gly Arg Lys Tyr Arg Gln Glu Leu Lys
    1340                1345                1350

Glu Met Arg Trp Glu Arg Glu His Gln Glu Arg Glu Pro Asp Glu
    1355                1360                1365

Thr Glu Asp Ile Lys Lys
    1370

<210> SEQ ID NO 3
<211> LENGTH: 412
<212> TYPE: PRT
<213> ORGANISM: Caenorhabditis elegans

<400> SEQUENCE: 3

Met Ser Leu Phe Asn Ile Met Lys Gly Thr Ser Gly Gly Glu Pro Ile
1               5                   10                  15
```

-continued

```
Leu His Asn Glu Arg Leu Glu Tyr Leu Gly Asp Ala Val Val Glu Leu
             20                  25                  30

Ile Val Ser His His Leu Tyr Phe Met Leu Thr His His Phe Glu Gly
             35                  40                  45

Gly Leu Ala Thr Tyr Arg Thr Ala Leu Val Gln Asn Arg Asn Leu Ala
             50                  55                  60

Thr Leu Ala Lys Asn Cys Arg Ile Asp Glu Met Leu Gln Tyr Ser His
 65                  70                  75                  80

Gly Ala Asp Leu Ile Asn Val Ala Glu Phe Lys His Ala Leu Ala Asn
                 85                  90                  95

Ala Phe Glu Ala Val Met Ala Ala Ile Tyr Leu Asp Gly Gly Leu Ala
            100                 105                 110

Pro Cys Asp Val Ile Phe Ser Lys Ala Met Tyr Gly His Gln Pro Val
            115                 120                 125

Leu Lys Glu Lys Trp Asp His Ile Asn Glu His Glu Leu Lys Arg Glu
            130                 135                 140

Asp Pro Gln Gly Asp Arg Asp Leu Ser Phe Ile Thr Pro Thr Leu Ser
145                 150                 155                 160

Thr Phe His Ala Leu Glu Glu Arg Leu Gly Ile Gln Phe Asn Asn Ile
                165                 170                 175

Arg Leu Leu Ala Lys Ala Phe Thr Arg Arg Asn Ile Pro Asn Asn Asp
            180                 185                 190

Leu Thr Lys Gly His Asn Gln Arg Leu Glu Trp Leu Gly Asp Ser Val
            195                 200                 205

Leu Gln Leu Ile Val Ser Asp Phe Leu Tyr Arg Arg Phe Pro Tyr His
            210                 215                 220

His Glu Gly His Met Ser Leu Leu Arg Thr Ser Leu Val Ser Asn Gln
225                 230                 235                 240

Thr Gln Ala Val Val Cys Asp Asp Leu Gly Phe Thr Glu Phe Val Ile
                245                 250                 255

Lys Ala Pro Tyr Lys Thr Pro Glu Leu Lys Leu Lys Asp Lys Ala Asp
            260                 265                 270

Leu Val Glu Ala Phe Ile Gly Ala Leu Tyr Val Asp Arg Gly Ile Glu
            275                 280                 285

His Cys Arg Ala Phe Ile Arg Ile Val Phe Cys Pro Arg Leu Lys His
            290                 295                 300

Phe Ile Glu Ser Glu Lys Trp Asn Asp Ala Lys Ser His Leu Gln Gln
305                 310                 315                 320

Trp Cys Leu Ala Met Arg Asp Pro Ser Ser Glu Pro Asp Met Pro
                325                 330                 335

Glu Tyr Arg Val Leu Gly Ile Glu Gly Pro Thr Asn Asn Arg Ile Phe
            340                 345                 350

Lys Ile Ala Val Tyr Tyr Lys Gly Lys Arg Leu Ala Ser Ala Ala Glu
            355                 360                 365

Ser Asn Val His Lys Ala Glu Leu Arg Val Ala Glu Leu Ala Leu Ala
370                 375                 380

Asn Leu Glu Ser Met Ser Phe Ser Lys Met Lys Ala Lys Asn Asn Ser
385                 390                 395                 400

Asn Met Arg Arg Arg Leu Glu Gln Asp Thr Ser Asp
                405                 410
```

<210> SEQ ID NO 4
<211> LENGTH: 366

```
<212> TYPE: PRT
<213> ORGANISM: Saccharomyces pombe

<400> SEQUENCE: 4

Met Gly Arg Phe Lys Arg His His Glu Gly Asp Ser Asp Ser Ser
1               5                   10                  15

Ser Ala Ser Asp Ser Leu Ser Arg Gly Arg Arg Ser Leu Gly His Lys
            20                  25                  30

Arg Ser His Ile Lys Asn Arg Gln Tyr Tyr Ile Leu Glu Lys Lys
        35                  40                  45

Ile Arg Lys Leu Met Phe Ala Met Lys Ala Leu Leu Glu Glu Thr Lys
50                  55                  60

His Ser Thr Lys Asp Asp Val Asn Leu Val Ile Pro Gly Ser Thr Trp
65                  70                  75                  80

Ser His Ile Glu Gly Val Tyr Glu Met Leu Lys Ser Arg His Asp Arg
                85                  90                  95

Gln Asn Glu Pro Val Ile Glu Glu Pro Ser Ser His Pro Lys Asn Gln
            100                 105                 110

Lys Asn Gln Glu Asn Asn Glu Pro Thr Ser Glu Glu Phe Glu Glu Gly
        115                 120                 125

Glu Tyr Pro Pro Pro Leu Pro Pro Leu Arg Ser Glu Lys Leu Lys Glu
    130                 135                 140

Gln Val Phe Met His Ile Ser Arg Ala Tyr Glu Ile Tyr Pro Asn Gln
145                 150                 155                 160

Ser Asn Pro Asn Glu Leu Leu Asp Ile His Asn Glu Arg Leu Glu Phe
                165                 170                 175

Leu Gly Asp Ser Phe Phe Asn Leu Phe Thr Thr Arg Ile Ile Phe Ser
            180                 185                 190

Lys Phe Pro Gln Met Asp Glu Gly Ser Leu Ser Lys Leu Arg Ala Lys
        195                 200                 205

Phe Val Gly Asn Glu Ser Ala Asp Lys Phe Ala Arg Leu Tyr Gly Phe
    210                 215                 220

Asp Lys Thr Leu Val Leu Ser Tyr Ser Ala Glu Lys Asp Gln Leu Arg
225                 230                 235                 240

Lys Ser Gln Lys Val Ile Ala Asp Thr Phe Glu Ala Tyr Leu Gly Ala
                245                 250                 255

Leu Ile Leu Asp Gly Gln Glu Glu Thr Ala Phe Gln Trp Val Ser Arg
            260                 265                 270

Leu Leu Gln Pro Lys Ile Ala Asn Ile Thr Val Gln Arg Pro Ile Asp
        275                 280                 285

Lys Leu Ala Lys Ser Lys Leu Phe His Lys Tyr Ser Thr Leu Gly His
    290                 295                 300

Ile Glu Tyr Arg Trp Pro Ala Cys Val Asp Gly Ala Gly Gly Ser Ala
305                 310                 315                 320

Glu Gly Tyr Val Ile Ala Cys Ile Phe Asn Gly Lys Glu Val Ala Arg
                325                 330                 335

Ala Trp Gly Ala Asn Gln Lys Asp Ala Gly Ser Arg Ala Ala Met Gln
            340                 345                 350

Ala Leu Glu Val Leu Ala Lys Asp Tyr Ser Lys Phe Ala Arg
        355                 360                 365

<210> SEQ ID NO 5
<211> LENGTH: 471
<212> TYPE: PRT
<213> ORGANISM: Saccharomyces cerevisiae
```

<400> SEQUENCE: 5

| | | | | | | | | | | | | | | |
|---|---|---|---|---|---|---|---|---|---|---|---|---|---|---|
|Met|Gly|Ser|Lys|Val|Ala|Gly|Lys|Lys|Thr|Gln|Asn|Asp|Asn|Lys|
|1| | | |5| | | | |10| | | | |15|

Leu Asp Asn Glu Asn Gly Ser Gln Gln Arg Glu Asn Ile Asn Thr Lys
              20                  25                  30

Thr Leu Leu Lys Gly Asn Leu Lys Ile Ser Asn Tyr Lys Tyr Leu Glu
        35                  40                  45

Val Ile Gln Leu Glu His Ala Val Thr Lys Leu Val Glu Ser Tyr Asn
   50                  55                  60

Lys Ile Ile Glu Leu Ser Pro Asn Leu Val Ala Tyr Asn Glu Ala Val
65                  70                  75              80

Asn Asn Gln Asp Arg Val Pro Val Gln Ile Leu Pro Ser Leu Ser Arg
              85                  90                  95

Tyr Gln Leu Lys Leu Ala Ala Glu Leu Lys Thr Leu His Asp Leu Lys
          100                  105               110

Lys Asp Ala Ile Leu Thr Glu Ile Thr Asp Tyr Glu Asn Glu Phe Asp
          115                  120               125

Thr Glu Gln Lys Gln Pro Ile Leu Gln Glu Ile Ser Lys Ala Asp Met
   130                  135                 140

Glu Lys Leu Glu Lys Leu Glu Gln Val Lys Arg Glu Lys Arg Glu Lys
145                 150                 155             160

Ile Asp Val Asn Val Tyr Glu Asn Leu Asn Glu Lys Glu Asp Glu Glu
              165              170              175

Glu Asp Glu Gly Glu Asp Ser Tyr Asp Pro Thr Lys Ala Gly Asp Ile
        180                  185              190

Val Lys Ala Thr Lys Trp Pro Pro Lys Leu Pro Glu Ile Gln Asp Leu
          195                200              205

Ala Ile Arg Ala Arg Val Phe Ile His Lys Ser Thr Ile Lys Asp Lys
   210                  215                 220

Val Tyr Leu Ser Gly Ser Glu Met Ile Asn Ala His Asn Glu Arg Leu
225                 230                 235              240

Glu Phe Leu Gly Asp Ser Ile Leu Asn Ser Val Met Thr Leu Ile Ile
              245              250              255

Tyr Asn Lys Phe Pro Asp Tyr Ser Glu Gly Gln Leu Ser Thr Leu Arg
        260                  265              270

Met Asn Leu Val Ser Asn Glu Gln Ile Lys Gln Trp Ser Ile Met Tyr
       275                  280              285

Asn Phe His Glu Lys Leu Lys Thr Asn Phe Asp Leu Lys Asp Glu Asn
   290                  295                 300

Ser Asn Phe Gln Asn Gly Lys Leu Lys Leu Tyr Ala Asp Val Phe Glu
305                 310                 315              320

Ala Tyr Ile Gly Gly Leu Met Glu Asp Pro Arg Asn Asn Leu Pro
              325              330              335

Lys Ile Arg Lys Trp Leu Arg Lys Leu Ala Lys Pro Val Ile Glu Glu
        340                  345              350

Ala Thr Arg Asn Gln Val Ala Leu Glu Lys Thr Asp Lys Leu Asp Met
       355                  360              365

Asn Ala Lys Arg Gln Leu Tyr Ser Leu Ile Gly Tyr Ala Ser Leu Arg
   370                  375                 380

Leu His Tyr Val Thr Val Lys Lys Pro Thr Ala Val Asp Pro Asn Ser
385                 390                 395              400

Ile Val Glu Cys Arg Val Gly Asp Gly Thr Val Leu Gly Thr Gly Val

```
                       405                 410                 415
Gly Arg Asn Ile Lys Ile Ala Gly Ile Arg Ala Ala Glu Asn Ala Leu
                420                 425                 430

Arg Asp Lys Lys Met Leu Asp Phe Tyr Ala Lys Gln Arg Ala Ala Ile
            435                 440                 445

Pro Arg Ser Glu Ser Val Leu Lys Asp Pro Ser Gln Lys Asn Lys Lys
        450                 455                 460

Arg Lys Phe Ser Asp Thr Ser
465                 470

<210> SEQ ID NO 6
<211> LENGTH: 226
<212> TYPE: PRT
<213> ORGANISM: Escherichia coli

<400> SEQUENCE: 6

Met Asn Pro Ile Val Ile Asn Arg Leu Gln Arg Lys Leu Gly Tyr Thr
1               5                   10                  15

Phe Asn His Gln Glu Leu Leu Gln Gln Ala Leu Thr His Arg Ser Ala
            20                  25                  30

Ser Ser Lys His Asn Glu Arg Leu Glu Phe Leu Gly Asp Ser Ile Leu
        35                  40                  45

Ser Tyr Val Ile Ala Asn Ala Leu Tyr His Arg Phe Pro Arg Val Asp
    50                  55                  60

Glu Gly Asp Met Ser Arg Met Arg Ala Thr Leu Val Arg Gly Asn Thr
65                  70                  75                  80

Leu Ala Glu Leu Ala Arg Glu Phe Glu Leu Gly Glu Cys Leu Arg Leu
                85                  90                  95

Gly Pro Gly Glu Leu Lys Ser Gly Gly Phe Arg Arg Glu Ser Ile Leu
            100                 105                 110

Ala Asp Thr Val Glu Ala Leu Ile Gly Gly Val Phe Leu Asp Ser Asp
        115                 120                 125

Ile Gln Thr Val Glu Lys Leu Ile Leu Asn Trp Tyr Gln Thr Arg Leu
    130                 135                 140

Asp Glu Ile Ser Pro Gly Asp Lys Gln Lys Asp Pro Lys Thr Arg Leu
145                 150                 155                 160

Gln Glu Tyr Leu Gln Gly Arg His Leu Pro Leu Pro Thr Tyr Leu Val
                165                 170                 175

Val Gln Val Arg Gly Glu Ala His Asp Gln Glu Phe Thr Ile His Cys
            180                 185                 190

Gln Val Ser Gly Leu Ser Glu Pro Val Val Gly Thr Gly Ser Ser Arg
        195                 200                 205

Arg Lys Ala Glu Gln Ala Ala Ala Glu Gln Ala Leu Lys Lys Leu Glu
    210                 215                 220

Leu Glu
225

<210> SEQ ID NO 7
<211> LENGTH: 11
<212> TYPE: PRT
<213> ORGANISM: Homo sapiens

<400> SEQUENCE: 7

His Asn Glu Arg Leu Glu Phe Leu Gly Asp Ser
1               5                   10
```

```
<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
atccctttct tccgcatgtg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
gccaaggcgt gacatgatat                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
cggatcatta aagagcaagc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tattcaccaa agagcttcgc                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
caatcgtgga aagaagcaga                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gctcccattt ccgcttgctg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic
```

-continued

```
<400> SEQUENCE: 14
atgctctctt tcccacctca                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
aaatactcca cacttgcatg                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
tgcacattca ccaaagtcaa                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
agtctagggt cacaatctgg                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ttcagttgta gtggtccgac                                                   20

<210> SEQ ID NO 19
<211> LENGTH: 40
<212> TYPE: DNA
<213> ORGANISM: Artificial Sequence
<220> FEATURE:
<223> OTHER INFORMATION: Synthetic

<400> SEQUENCE: 19
caaggcacgc ctctcagatc gctagagaag gcttttctca                             40

<210> SEQ ID NO 20
<211> LENGTH: 40
<212> TYPE: DNA
<213> ORGANISM: Artificial Sequence
<220> FEATURE:
<223> OTHER INFORMATION: Synthetic

<400> SEQUENCE: 20
cattaattct cgcagctagc gctgcgttct tcatcgacgc                             40

<210> SEQ ID NO 21
<211> LENGTH: 35
```

```
<212> TYPE: DNA
<213> ORGANISM: Artificial Sequence
<220> FEATURE:
<223> OTHER INFORMATION: Synthetic

<400> SEQUENCE: 21
ccaaatactg atcgacaact tattgaaact tctcc                              35

<210> SEQ ID NO 22
<211> LENGTH: 37
<212> TYPE: DNA
<213> ORGANISM: Artificial Sequence
<220> FEATURE:
<223> OTHER INFORMATION: Synthetic

<400> SEQUENCE: 22
gagtttgaag aagcaattgg agtaattttt actcatg                            37

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
tcgacttctg gcaagggcat tcacatt                                       27

<210> SEQ ID NO 24
<211> LENGTH: 26
<212> TYPE: DNA
<213> ORGANISM: Artificial Sequence
<220> FEATURE:
<223> OTHER INFORMATION: Synthetic

<400> SEQUENCE: 24
cctctgtgcc agcttctgtt tgtcag                                        26

<210> SEQ ID NO 25
<211> LENGTH: 26
<212> TYPE: DNA
<213> ORGANISM: Artificial Sequence
<220> FEATURE:
<223> OTHER INFORMATION: Synthetic

<400> SEQUENCE: 25
tgtcagtttg tttgactttg ggacta                                        26

<210> SEQ ID NO 26
<211> LENGTH: 26
<212> TYPE: DNA
<213> ORGANISM: Artificial Sequence
<220> FEATURE:
<223> OTHER INFORMATION: Synthetic

<400> SEQUENCE: 26
tttgctagga ggtggcgaag tttcac                                        26

<210> SEQ ID NO 27
<211> LENGTH: 30
<212> TYPE: DNA
<213> ORGANISM: Artificial Sequence
<220> FEATURE:
<223> OTHER INFORMATION: Synthetic

<400> SEQUENCE: 27
```
gcttgatggc ctcttctcca ggataaatgc                                      30

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
aatgctgtgc ctaattcctg tgcgtcttgc                                      30

<210> SEQ ID NO 29
<211> LENGTH: 48
<212> TYPE: DNA
<213> ORGANISM: Artificial Sequence
<220> FEATURE:
<223> OTHER INFORMATION: Synthetic

<400> SEQUENCE: 29
caggtgctgt cctcatcaga ctcacactcg gattcactgg aactctct                  48

<210> SEQ ID NO 30
<211> LENGTH: 26
<212> TYPE: DNA
<213> ORGANISM: Artificial Sequence
<220> FEATURE:
<223> OTHER INFORMATION: Synthetic

<400> SEQUENCE: 30
cactgggcag gaaagaacta gggttg                                          26

<210> SEQ ID NO 31
<211> LENGTH: 26
<212> TYPE: DNA
<213> ORGANISM: Artificial Sequence
<220> FEATURE:
<223> OTHER INFORMATION: Synthetic

<400> SEQUENCE: 31
tggaaactat taaaactggg aggtgg                                          26

<210> SEQ ID NO 32
<211> LENGTH: 50
<212> TYPE: DNA
<213> ORGANISM: Artificial Sequence
<220> FEATURE:
<223> OTHER INFORMATION: Synthetic

<400> SEQUENCE: 32
aggcatggag ggaggggggca tcatgaaggg gaaagtgcct tgtccaggag               50

<210> SEQ ID NO 33
<211> LENGTH: 40
<212> TYPE: DNA
<213> ORGANISM: Artificial Sequence
<220> FEATURE:
<223> OTHER INFORMATION: Synthetic

<400> SEQUENCE: 33
caaggcacgc ctctcagatc gctagagaag gcttttctca                           40

<210> SEQ ID NO 34
<211> LENGTH: 40
<212> TYPE: DNA
<213> ORGANISM: Artificial Sequence

```
<220> FEATURE:
<223> OTHER INFORMATION: Synthetic

<400> SEQUENCE: 34
cattaattct cgcagctagc gctgcgttct tcatcgacgc                    40

<210> SEQ ID NO 35
<211> LENGTH: 20
<212> TYPE: PRT
<213> ORGANISM: Homo sapiens

<400> SEQUENCE: 35

Cys Arg Ser Asp Tyr Asp Arg Gly Arg Thr Pro Ser Arg His Arg Ser
1               5                   10                  15

Tyr Glu Arg Ser
            20

<210> SEQ ID NO 36
<211> LENGTH: 20
<212> TYPE: PRT
<213> ORGANISM: Homo sapiens

<400> SEQUENCE: 36

Cys Arg Trp Glu Arg Glu His Gln Glu Arg Glu Pro Asp Glu Thr Glu
1               5                   10                  15

Asp Ile Lys Lys
            20
```